United States Patent
Hashemi

(10) Patent No.: US 11,998,880 B2
(45) Date of Patent: Jun. 4, 2024

(54) COLLAPSIBLE AGITATOR ASSEMBLY FOR A BIOPROCESSING SYSTEM

(71) Applicant: GLOBAL LIFE SCIENCES SOLUTIONS USA LLC, Marlborough, MA (US)

(72) Inventor: Nasim Hashemi, Marlborough, MA (US)

(73) Assignee: GLOBAL LIFE SCIENCES SOLUTIONS USA LLC, Marlborough, MA (US)

( * ) Notice: Subject to any disclaimer, the term of this patent is extended or adjusted under 35 U.S.C. 154(b) by 475 days.

(21) Appl. No.: 17/008,986

(22) Filed: Sep. 1, 2020

(65) Prior Publication Data

US 2022/0062836 A1    Mar. 3, 2022

(51) Int. Cl.
*B01F 27/2124*    (2022.01)
*B01F 27/054*     (2022.01)
*B01F 27/192*     (2022.01)
*B01F 27/88*      (2022.01)
*B01F 35/513*     (2022.01)
*C12M 1/06*       (2006.01)
*B01F 101/44*     (2022.01)

(52) U.S. Cl.
CPC ...... *B01F 27/0541* (2022.01); *B01F 27/1921* (2022.01); *B01F 27/2124* (2022.01); *B01F 27/88* (2022.01); *B01F 35/513* (2022.01); *C12M 27/02* (2013.01); *B01F 2101/44* (2022.01)

(58) Field of Classification Search
CPC .................................. B01F 27/2124
USPC ........................ 366/273, 274, 286
See application file for complete search history.

(56) References Cited

U.S. PATENT DOCUMENTS

| | | | | | |
|---|---|---|---|---|---|
| 905,302 | A | * | 12/1908 | Fleming | B01F 35/00 366/164.4 |
| 1,065,806 | A | * | 6/1913 | Hollingsworth | B01F 27/806 403/59 |
| 2,817,503 | A | * | 12/1957 | Hahn | A47J 43/044 74/110 |
| 4,737,036 | A | * | 4/1988 | Offermann | A47J 43/1081 366/256 |
| 8,870,443 | B2 | * | 10/2014 | Greller | B01F 27/2122 366/102 |
| 10,118,141 | B2 | * | 11/2018 | Larsen | B01F 33/86 |
| 10,456,761 | B2 | * | 10/2019 | Chaussin | C12M 23/26 |
| 2011/0013474 | A1 | * | 1/2011 | Ludwig | C12M 29/06 366/140 |
| 2011/0026360 | A1 | | 2/2011 | Greller et al. | |
| 2018/0057787 | A1 | | 3/2018 | Friedman et al. | |

(Continued)

FOREIGN PATENT DOCUMENTS

| CN | 108 672 280 | 10/2018 |
| DE | 20 2007 005868 | 7/2007 |
| WO | 2015039034 | 3/2015 |

OTHER PUBLICATIONS

Invitation to pay additional fees issued in corresponding PCT Application No. PCT/EP2021/072345 dated Nov. 11, 2021.

*Primary Examiner* — David L Sorkin
(74) *Attorney, Agent, or Firm* — Grogan, Tuccillo & Vanderleeden LLP

(57) ABSTRACT

A mixing system includes a container for containing a fluid, and an agitator assembly disposable in the container for mixing the fluid. The agitator includes an extensible shaft and at least one impeller connected to the extensible shaft.

13 Claims, 7 Drawing Sheets

(56) References Cited

U.S. PATENT DOCUMENTS

| | | |
|---|---|---|
| 2018/0071700 A1 | 3/2018 | Staheli et al. |
| 2018/0221838 A1 | 8/2018 | Chaussin et al. |
| 2019/0329197 A1 | 10/2019 | Chaussin et al. |
| 2021/0077959 A1* | 3/2021 | Graham ............ B01F 27/11251 |

* cited by examiner

COLLAPSIBLE AGITATOR ASSEMBLY FOR A BIOPROCESSING SYSTEM

BACKGROUND

Technical Field

Embodiments of the invention relate generally to bioprocessing systems and methods and, more particularly, to a collapsible agitator assembly for single-use bioreactor systems.

Discussion of Art

A variety of vessels, devices, components and unit operations are known for carrying out biochemical and/or biological processes and/or manipulating liquids and other products of such processes. In order to avoid the time, expense, and difficulties associated with sterilizing the vessels used in biopharmaceutical manufacturing processes, single-use or disposable bioreactor bags and single-use mixer bags are used as such vessels. For instance, biological materials (e.g., animal and plant cells) including, for example, mammalian, plant or insect cells and microbial cultures can be processed using disposable or single-use mixers and bioreactors.

Increasingly, in the biopharmaceutical industry, single use or disposable containers are used. Such containers can be flexible or collapsible plastic bags that are supported by an outer rigid structure such as a stainless steel shell or vessel. Use of sterilized disposable bags eliminates time-consuming step of cleaning of the vessel and reduces the chance of contamination. The bag may be positioned within the rigid vessel and filled with the desired fluid for mixing. An agitator assembly disposed within the bag is used to mix the fluid. Existing agitators are either top-driven (having a shaft that extends downwardly into the bag, on which one or more impellers are mounted) or bottom-driven (having an impeller disposed in the bottom of the bag that is driven by a magnetic drive system or motor positioned outside the bag and/or vessel). Most magnetic agitator systems include a rotating magnetic drive head outside of the bag and a rotating magnetic agitator (also referred to in this context as the "impeller") within the bag. The movement of the magnetic drive head enables torque transfer and thus rotation of the magnetic agitator allowing the agitator to mix a fluid within the vessel. Magnetic coupling of the agitator inside the bag, to a drive system or motor external to the bag and/or bioreactor vessel, can eliminate contamination issues, allow for a completely enclosed system, and prevent leakage. Because there is no need to have a drive shaft penetrate the bioreactor vessel wall to mechanically spin the agitator, magnetically coupled systems can also eliminate the need for having seals between the drive shaft and the vessel.

In the design of the single-use bioreactors, package size of the unfolded, flexible bag is an important consideration. Therefore, in most existing single-use bioreactors a single bottom-mounted impeller (with no shaft) has been employed, allowing the flexible bag and impeller to be packed into a compact unit that can be placed directly into a supporting vessel with minimal operator manipulation. Once a shaft has been eliminated from the design, the agitator/impeller is limited to having just one impeller locating near the bottom of the vessel. As a result, in comparison with traditional stainless-steel bioreactors, single use systems have lower mass transfer rate, longer mixing time, and non-uniform distributions of the shear rates within the tank.

Existing efforts to address these issues have involved the use of foldable shafts, which have shown undesirable instability especially at high impeller rotation speeds, which affect the mixing performance of the system.

In view of the above, there is a need for an agitator assembly for a single-use bioprocessing system that can be collapsed for compact for storage and transport, and which can be expanded for use to provide for optimal gas residence times, decreased mixing times, lower mass transfer rates, and uniform shear rate distribution typically provided by conventional, shaft-mounted agitator assemblies.

BRIEF DESCRIPTION

In an embodiment, a mixing system is provided. The mixing system includes a container for containing a fluid, and an agitator assembly disposable in the container for mixing the fluid. The agitator includes an extensible shaft and at least one impeller connected to the extensible shaft.

In another embodiment, an agitator assembly for a mixing system is provided. The agitator assembly includes a first shaft segment, a second shaft segment telescopically connected to the first shaft segment, and an impeller connected to the second shaft segment. The second shaft segment and impeller are moveable from a first position in which the second shaft segment is nested with the first shaft segment, and a second position in which the second shaft segment extends from the first shaft segment.

In yet another embodiment, a method for bioprocessing is provided. The method includes the steps of positioning a flexible bioprocessing bag inside a support vessel, the flexible bioprocessing bag containing an agitator assembly positioned at a bottom of the flexible bioprocessing bag, the agitator assembly including a hub, an extensible shaft connected to the hub, and an impeller connected to the extensible shaft, placing a hub of the agitator assembly in registration with a magnetic drive assembly exterior to the flexible bioprocessing bag, and extending the extensible shaft from a first position where the impeller is located a first distance from the bottom of the flexible bioprocessing bag, to a second position where the impeller is located a second distance from the bottom of the flexible bioprocessing bag, wherein the second distance is greater than the first distance.

DRAWINGS

The present invention will be better understood from reading the following description of non-limiting embodiments, with reference to the attached drawings, wherein below:

DETAILED DESCRIPTION

Figure 1:
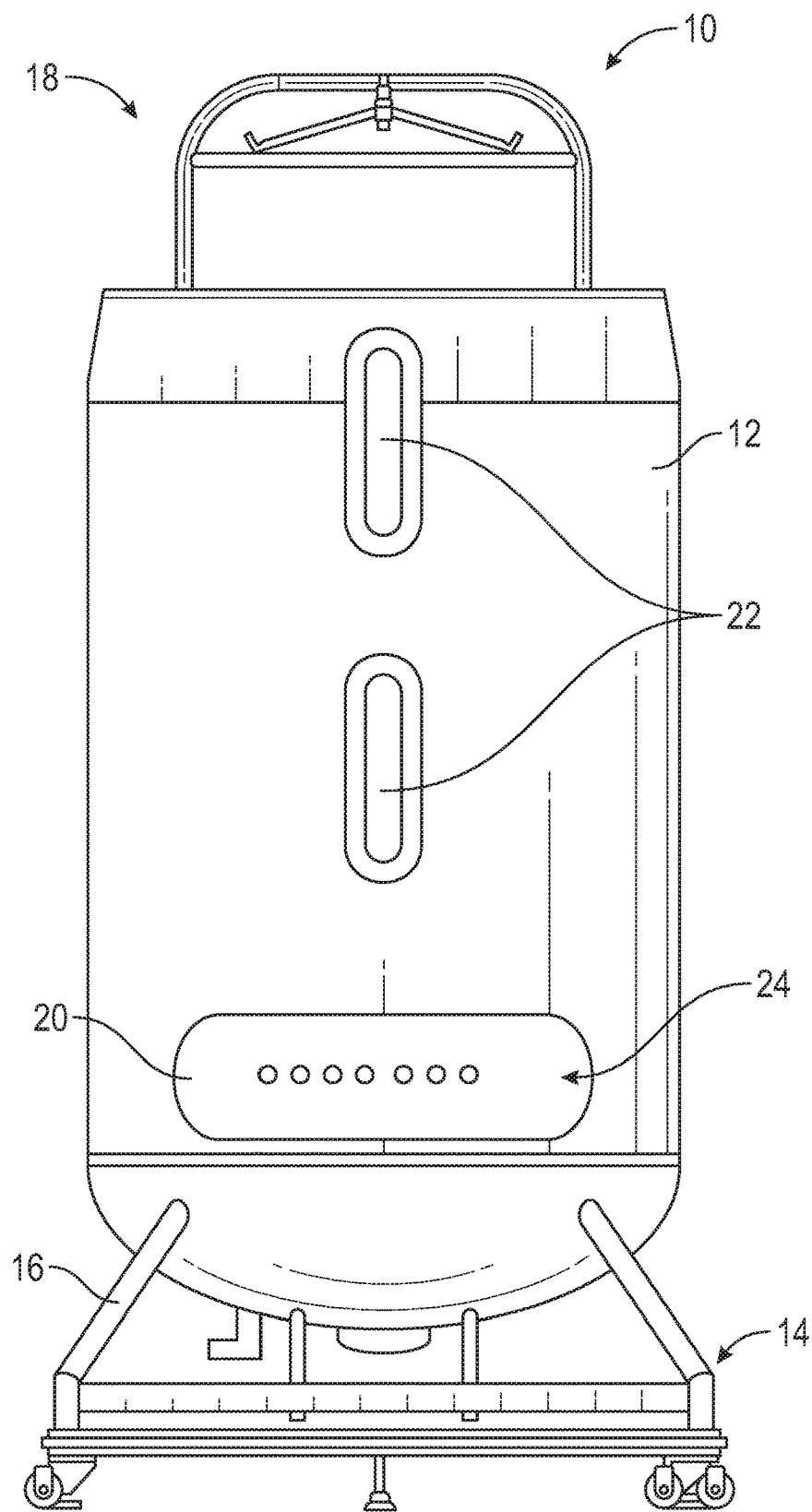
FIG. 1 is a front elevational view of a bioprocessing system according to an embodiment of the invention.

Reference will be made below in detail to exemplary embodiments of the invention, examples of which are illustrated in the accompanying drawings. Wherever possible, the same reference characters used throughout the drawings refer to the same or like parts.

As used herein, the term "flexible" refers to a structure or material that is pliable, or capable of being bent without breaking, and may also refer to a material that is compressible or expandable. An example of a flexible structure is a bag formed of polyethylene film. The terms "rigid" and "semi-rigid" are used herein interchangeably to describe structures that are "non-collapsible," that is to say structures that do not fold, collapse, or otherwise deform under normal forces to substantially reduce their elongate dimension. Depending on the context, "semi-rigid" can also denote a structure that is more flexible than a "rigid" element, e.g., a bendable tube or conduit, but still one that does not collapse longitudinally under normal conditions and forces.

A "vessel," as the term is used herein, means a flexible bag, a flexible container, a semi-rigid container, a rigid container, or a flexible or semi-rigid tubing, as the case may be. The term "vessel" as used herein is intended to encompass bioreactor vessels having a wall or a portion of a wall that is flexible or semi-rigid, single use flexible bags, as well as other containers or commonly used in biological or biochemical processing, including, for example, cell culture/purification systems, mixing systems, media/buffer preparation systems, and filtration/purification systems, e.g., chromatography and tangential flow filter systems, and their associated flow paths. As used herein, the term "bag" means a flexible or semi-rigid container or vessel used, for example, as a bioreactor or mixer for the contents within.

Embodiments of the invention provide bioreactor systems and mixing systems including agitator assemblies for a bioreactor system. In an embodiment, a mixing system includes a container for containing a fluid, and an agitator assembly disposable in the container for mixing the fluid. The agitator includes an extensible shaft and at least one impeller connected to the extensible shaft. The extensible shaft is moveable between a first position in which the at least one impeller is spaced a first distance from a bottom of the container and a second position in which the at least one impeller is spaced a second distance from the bottom of the container, wherein the second distance is greater than the first distance. In an embodiment, the extensible shaft includes a first shaft segment and a second shaft segment telescopically connected to the first shaft segment, wherein the at least one impeller is connected to the second shaft segment.

Figure 2:
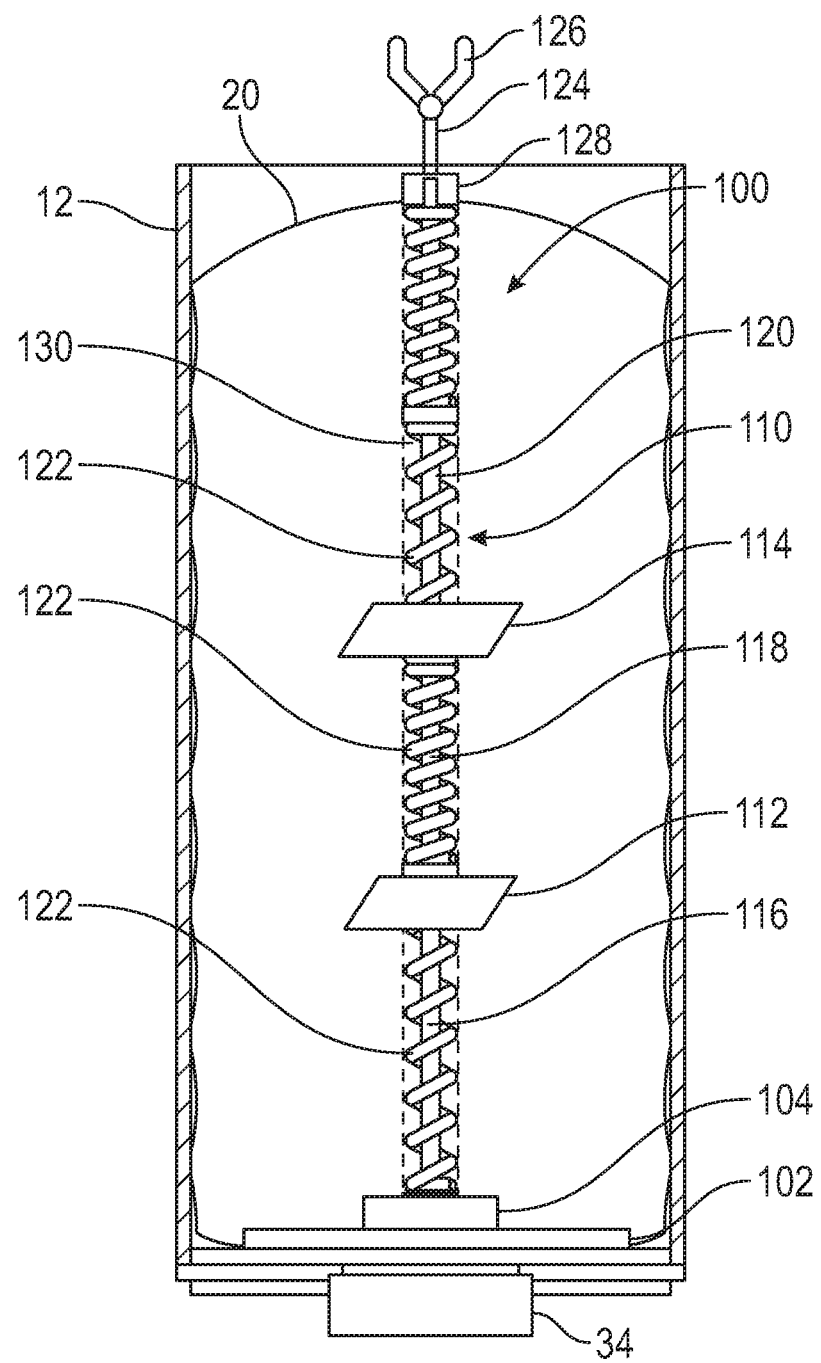
FIG. 2 is a simplified side elevational, cross-sectional view of the bioprocessing system of FIG. 1, showing a collapsible agitator assembly positioned therein.

With reference to FIGS. 1 and 2, a bioprocessing system 10 (also referred to herein as bioreactor system 10) according to an embodiment of the invention is illustrated. The bioreactor system 10 includes a generally rigid bioreactor vessel or support structure 12 mounted atop a base 14 having a plurality of legs 16. The vessel 12 may be formed, for example, from stainless steel, polymers, composites, glass, or other metals, and may be cylindrical in shape, although other shapes may also be utilized without departing from the broader aspects of the invention. The vessel 12 may be outfitted with a lift assembly 18 that provides support to a single-use, flexible bag 20 disposed within the vessel 12. The vessel 12 can be any shape or size as long as it is capable of supporting a single-use flexible bioreactor bag 20. For example, according to one embodiment of the invention the vessel 12 is capable of accepting and supporting a 10-2000 L flexible or collapsible bioprocess bag assembly 20.

The vessel 12 may include one or more sight windows 22, which allows one to view a fluid level within the flexible bag 20, as well as a window 24 positioned at a lower area of the vessel 12. The window 24 allows access to the interior of the vessel 12 for insertion and positioning of various sensors and probes (not shown) within the flexible bag 20, and for connecting one or more fluid lines to the flexible bag 20 for fluids, gases, and the like, to be added or withdrawn from the flexible bag 20. Sensors/probes and controls for monitoring and controlling important process parameters include any one or more, and combinations of: temperature, pressure, pH, dissolved oxygen (DO), dissolved carbon dioxide ($pCO_2$), mixing rate, and gas flow rate, for example.

With specific reference to FIG. 2, a schematic side elevational, cutaway view of the bioreactor system 10 is illustrated. As shown therein, the single-use, flexible bag 20 is disposed within the vessel 12 and restrained thereby. In embodiments, the single-use, flexible bag 20 is formed of a suitable flexible material, such as a homopolymer or a copolymer. The flexible material can be one that is USP Class VI certified, for example, silicone, polycarbonate, polyethylene, and polypropylene. Non-limiting examples of flexible materials include polymers such as polyethylene (for example, linear low density polyethylene and ultra-low density polyethylene), polypropylene, polyvinylchloride, polyvinyldichloride, polyvinylidene chloride, ethylene vinyl acetate, polycarbonate, polymethacrylate, polyvinyl alcohol, nylon, silicone rubber, other synthetic rubbers and/or plastics. In an embodiment, the flexible material may be a laminate of several different materials such as, for example Fortem™, Bioclear™ 10 and Bioclear 11 laminates, available from GE Healthcare Life Sciences. Portions of the flexible container can comprise a substantially rigid material such as a rigid polymer, for example, high density polyethylene, metal, or glass. The flexible bag may be supplied pre-sterilized, such as using gamma irradiation.

In an embodiment, the flexible bag 20 contains a mixing system having a collapsible agitator assembly 100. As shown therein, the agitator assembly 100 includes an impeller plate 102 positioned at the bottom center of the inside of the bag, and a magnetic hub 104 which rotates on the impeller plate 102. A magnetic drive 34 of the mixing system external to the vessel 12 provides the motive force for rotating the magnetic hub 104 to mix the contents of the flexible bag 20, as described hereinafter. While FIG. 2 illustrates the use of a magnetically-driven impeller/agitator, other types of agitators and drive systems are also possible, including mechanically-driven agitators.

Figure 3:
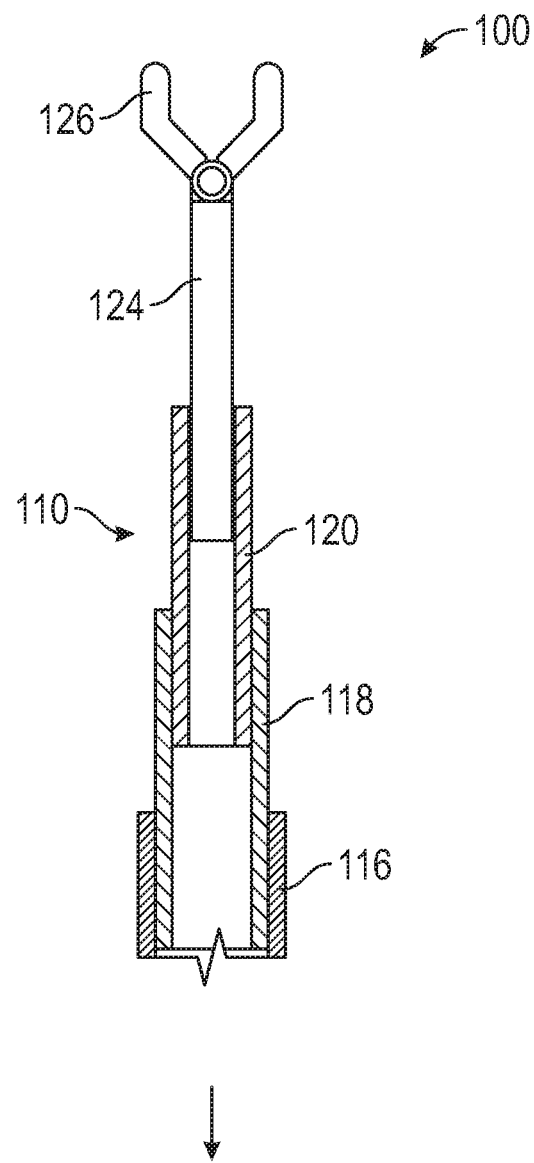
FIG. 3 is a side, cross-sectional view of a portion of the collapsible agitator assembly.
Figure 3:
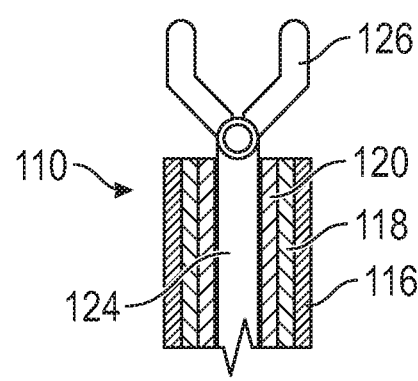

As further shown in FIG. 2, the agitator assembly 100 includes an extensible/collapsible shaft 110 mounted to the magnetic hub 104 and configured for rotation therewith, and at least one impeller, and in some embodiments, a plurality of impellers 112, 114, connected to the shaft 110. In an embodiment, the shaft 110 includes a plurality of shaft segments telescopically connected to one another (e.g., a first shaft segment 116, a second shaft segment 118, and a third shaft segment 120). For example, as best shown in FIG. 3, the second shaft segment 118 is nestably and telescopically connected to the first shaft segment 116, while the third shaft segment 120 is nestably and telescopically connected to the second shaft segment 118. The first impeller 112 is affixed to the first shaft segment 116 and moveable therewith, while the second impeller 114 is affixed to the second shaft segment 118 (or third shaft segment 120) and moveable therewith.

While FIGS. 2 and 3 show the agitator assembly 100 as including three shaft segments and two impellers, more or fewer than three shaft segments, and more or fewer than two impellers may be employed without departing from the broader aspects of the invention. Moreover, while the first shaft segment 116 is depicted as having a larger inner diameter than the second shaft segment 118 for receiving the smaller diameter second shaft segment 118, and the second shaft segment 118 is depicted as having a larger inner diameter than the third shaft segment 120 for receiving the smaller diameter third shaft segment 120, in an embodiment, the configuration may be reversed such that the second shaft segment 118 is telescopically and slidably received by the third shaft segment 120, and the first shaft segment 116 is telescopically and slidably received by the second shaft segment 118.

With further reference to FIG. 2, in an embodiment, each of the shaft segments 116, 118, 120 includes an associated biasing element/spring element, such as a coil spring 122, that is configured to bias the shaft segments 116, 118, 120 to their respective extended positions, as shown in FIGS. 2 and 3. In an embodiment, the spring element(s) may be disposed so as to surround the shaft segments. In other embodiments, the spring elements(s) may be housed within the shaft segments to ensure that the spring elements are not exposed to the surrounding environment within the bioprocessing bag. As also shown therein, the shaft 110 further includes a connecting or mounting shaft 124 extending from the uppermost shaft segment 120, and a connecting member 126 on the end of the connecting shaft 124. The connecting shaft 124 extends through a bushing or seal 128 in the top of the flexible bioreactor bag 20. The connecting member 126 is configured for connection to a supporting structure (not shown) positioned above the bioreactor vessel 12, to provide stability and support for the agitator assembly 100 during operation. In other embodiments, however, the connecting shaft and connecting member 126 may be omitted, such that the agitator assembly 100 is only supported on the impeller plate 102 (i.e., freestanding within the flexible bag 20). While FIG. 2 illustrates use of a coil spring 122 to bias the segments to their respective extended positions, it is contemplated that other biasing means may also be utilized to accomplish a similar function. For example, in an embodiment, the biasing element may be a hydraulic actuator, leaf spring, magnetic biasing element or other types of biasing elements known in the art.

With continued reference to FIG. 2, in an embodiment, the connecting shaft 124 and connecting member 128 are omitted, and the uppermost shaft segment is rotatably mounted to a bushing (e.g. bushing 128) positioned entirely within the bag 20 (e.g., mounted to an insider, top surface of the bag). In this respect, the entire agitator assembly 100 would thus be contained within the bag 20 (with no component extending though the bag 20), which ensures that sterility is maintained.

Figure 4:
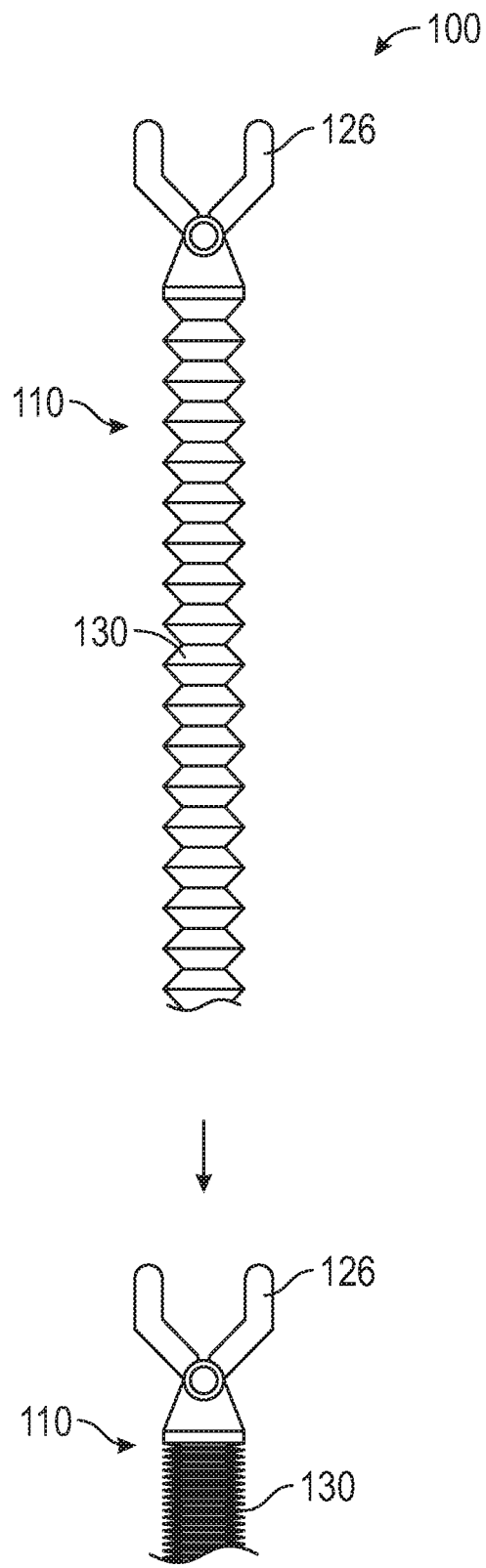
FIG. 4 is a side elevational view of a portion of the collapsible agitator assembly.

With reference to FIGS. 1 and 4, in an embodiment the agitator assembly 100 further includes a flexible sleeve or bellows 130 that encases the shaft 110 and the spring element(s) 122 to prevent fluid within the bag 20 from contacting the shaft segments or the spring element(s) 122.

As best shown in FIG. 4, the flexible bellows 130 is extendable and collapsible along with the shaft 110.

In operation, as best shown in FIG. 3, the shaft 110 is moveable between an extended position (top portion of FIGS. 3 and 4) and a collapsed position (bottom portion of FIGS. 3 and 4). As will be appreciated, in the collapsed position, at least the impeller 114 (not shown in FIG. 3 or 4) mounted to the second shaft segment 118 is spaced a first distance from a bottom of the flexible bag 20 when the shaft 110 is in the collapsed position, and is spaced a second distance from the bottom of the flexible bag 20 when the shaft 110 is in the extended position, wherein the second distance is greater than the first distance. Thus, when the shaft 110 is extended, the second impeller 114 connected to the second shaft segment 118 extends upwardly with the second shaft segment 118 to position the impeller 114 at a position spaced from the bottom of the bag 20.

In an embodiment, the agitator assembly 100 may deployed from the collapsed position to the extended position manually, for example, by grasping the connecting member 126 or connecting shaft and pulling moving the shaft 110 to the extended position. The connecting member 126 may then be connected to a support structure above the bioreactor vessel 12. In an embodiment, a locking mechanism may be deployed to maintain the shaft 110 in the extended position. For example, the locking mechanism may be the connecting member 126 that engages a support structure. In other embodiments, the locking mechanism may be a bayonet style locking mechanism on the shaft segments or spring latches, as described below, although other locking mechanisms may also be utilized without departing from the broader aspects of the invention.

Figure 5:
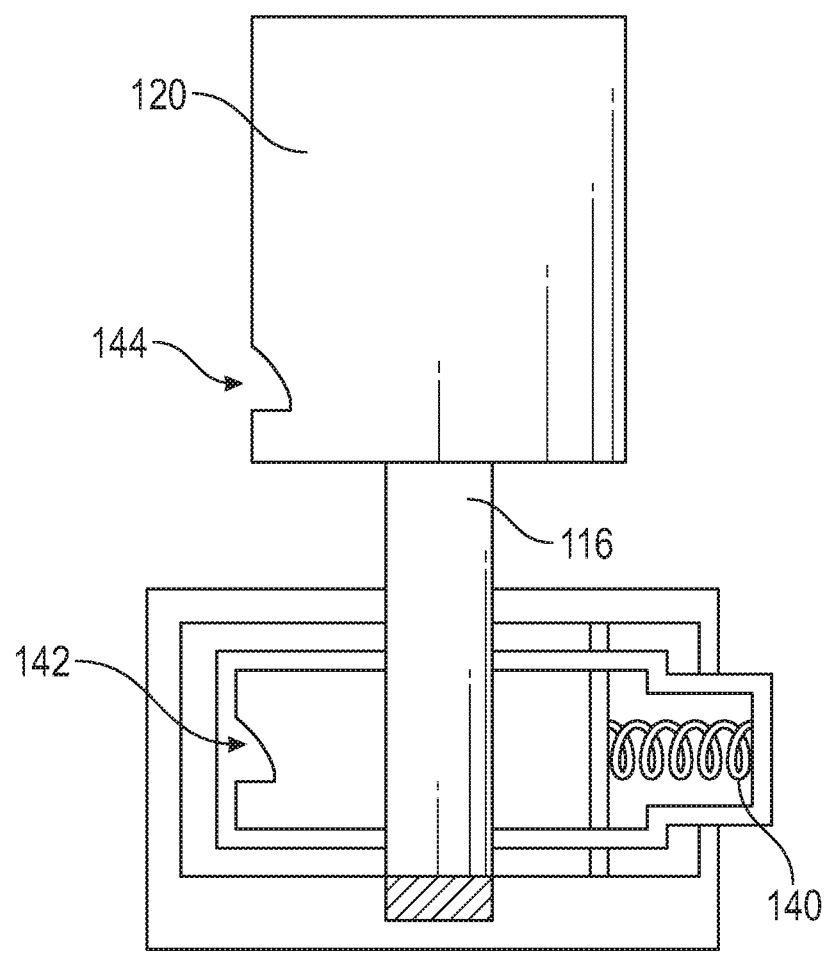
FIG. 5 is a simplified side elevational view showing an actuator mechanism of the collapsible agitator assembly.
Figure 6:
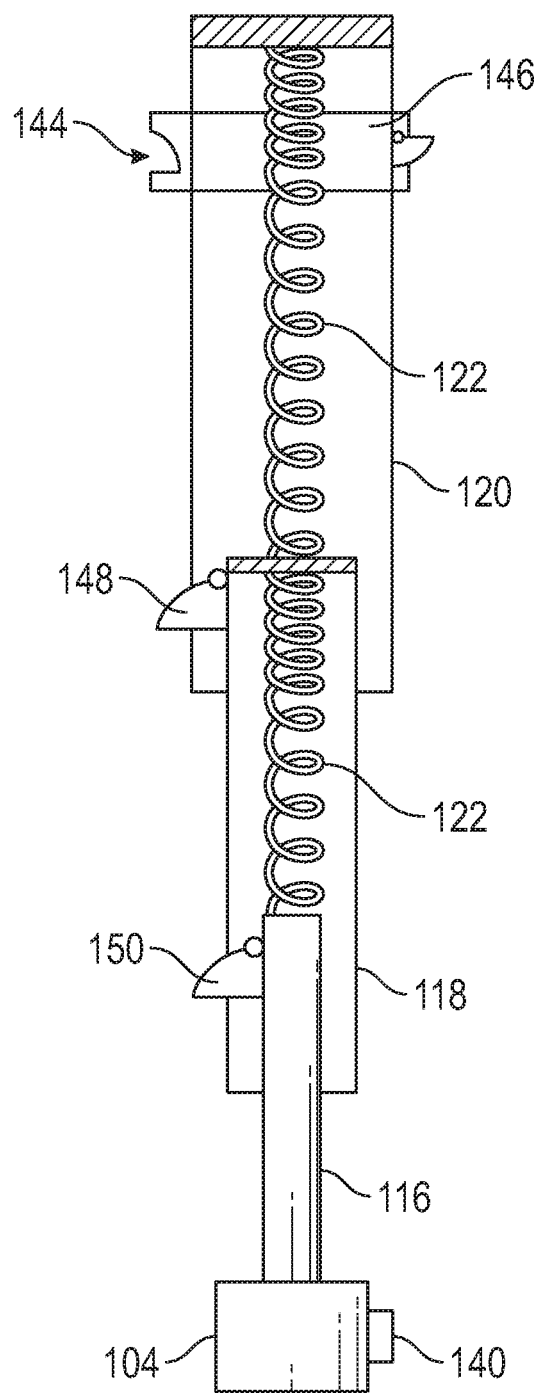
FIG. 6 is a simplified side elevational view showing an actuator and locking mechanism of the collapsible agitator assembly.

Turning now to FIGS. 5 and 6, in another embodiment, the agitator assembly 100 includes an actuator configured to automatically effect movement of the shaft 110 from the collapsed position to the extended position, and a locking mechanism configured to retain the shaft 110 in the extended position. As shown therein, for example, in an embodiment, the magnetic hub 104 may include an actuator in the form of a spring-biased release button 140 having a protrusion 142 that is configured to be received in a recess or slot 144 in a rider 146 mounted to the uppermost shaft segment (e.g., shaft segment 120). In such position, the spring element(s) 122 are compressed and the shaft 110 is in its collapsed position, and engagement of the protrusion 142 of the release button actuator 140 with the recess 144 in the rider 146 maintains the shaft 110 in such collapsed position. To extend the shaft 110 to its extended/deployed position, a user presses the release button 140. This causes the protrusion 142 located in the rear of the release button 140, to move out of the recess 144 located on the rider 146. The rider 146, and thus the shaft segments 118, 120 are free to move away from magnetic hub 104 and first shaft segment 116 under bias of the spring element(s) 122. Because the shaft segments 116, 118, 120 are all interconnected, the shaft 110 springs into its full length.

It is contemplated that other actuator mechanisms may also be employed to effect extension of the shaft 110 from its retracted position to its extended position. For example, in an embodiment, the actuator mechanism may be a retractable pen, bayonet connector or similar mechanism that provides for extension of the shaft 110 by applying an axial or rotational force to the shaft 110 from the top of the bag.

As shown in FIG. 6, and as alluded to above, in an embodiment, one or more of the shaft segments 116, 118, 120 include spring latches 148, 150. During the extending movement of the shaft 110, the spring latches 148, 150 spring outwardly to secure the telescoping mechanism (i.e., to maintain the shaft segments in their respective extended positions) and prevent it from recompression. In particular, once in the fully extended positions, the spring latches extend outwardly, preventing the shaft segments from being moved back to their nested configuration (due to contact of the spring latch of an upper segment with the upper end of a lower shaft segment). It is contemplated, however, that other locking mechanisms for preventing re-nesting of the shaft segments may be utilized such as, for example, a mechanism similar to that utilized in a retractable pen.

Figure 7:
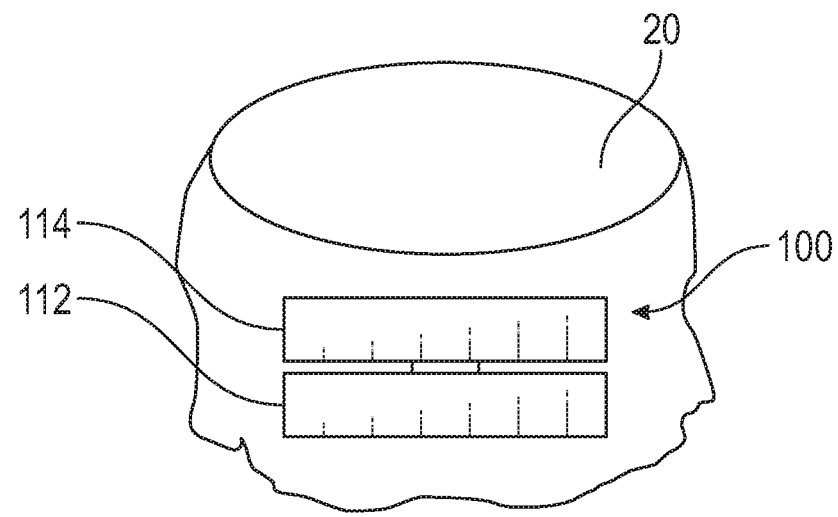
FIG. 7 is a simplified perspective illustration of a flexible bioprocessing bag having a collapsible agitator assembly, showing the agitator assembly in a collapsed configuration.
Figure 8:
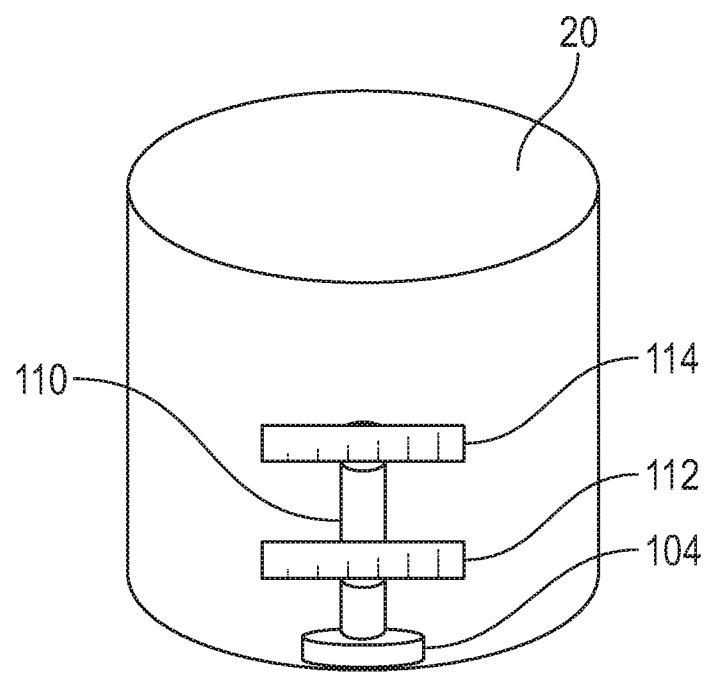
FIG. 8 is a simplified perspective illustration of a flexible bioprocessing bag having a collapsible agitator assembly, showing the agitator assembly in an expanded configuration.

Turning finally to FIGS. 7 and 8, schematic illustrations of the agitator assembly 100 deployed in a flexible bag 10 are shown. As shown in FIG. 7, the agitator assembly may be positioned within the bag in the collapsed position (where the shaft segments are nested with one another, the spring element(s) 122 are compressed, and actuator 140 maintains the agitator assembly in such collapsed position). In this state, the flexible bag can be folded and packaged for transport and storage. With reference to FIG. 8, in use, the flexible bag 20 can be unpackaged and placed within a bioreactor vessel 12, at which time the shaft 110 may be moved to its extended position to position the impellers 112, 114 at spaced vertical locations within the flexible bag 20 (i.e., either manually or via actuation of the actuator button 140).

The mixing system and agitator assembly of the invention therefore allows for multiple bottom, magnetically-driven impellers to be utilized in a single bioreactor vessel, while at the same time providing for a reduction in the size of the bioprocessing bag package (i.e., flexible bag and agitator assembly) for transport and storage. Indeed, the collapsible agitator assembly allows the bioprocessing bag 20 and agitator assembly 100 to be packaged into a compact unit that can be placed directly into the hardware (i.e., the bioreactor vessel 12) with minimal operation manipulation. This is particularly beneficial for large volume bioprocessing bags/vessels such as, for example, 2000 L and similarly-sized vessels, and where multiple impellers are advantageous such as in the culturing of shear-sensitive cells. In addition, the agitator assembly 100 of the invention, with the ability to locate impellers at various vertically-spaced locations within the bioprocessing bag, provides for better gas dispersion, decreases mixing time, and provides a more uniform distribution of shear rate throughout the processing volume, as compared to shaftless impellers typically used in single-use bioprocessing bag applications. Accordingly, the performance of the bioprocessing system, as a whole is increased.

The agitator assembly disclosed herein also allows for deployment of the agitator assembly from the collapsed position to the extended, operational position from outside the bag 20, so as to not compromise the sterile environment within the bag 20. Moreover, in addition to helping extend the shaft 110, the spring element(s) additionally help stabilize the shaft 110, particularly at high rotational speeds. The collapsible agitator assembly of the invention therefore overcomes a number of challenges associated with conventional single-use bioreactor vessels.

In an embodiment, a mixing system is provided. The mixing system includes a container for containing a fluid, and an agitator assembly disposable in the container for mixing the fluid. The agitator includes an extensible shaft and at least one impeller connected to the extensible shaft. In an embodiment, the extensible shaft is moveable between a first position in which the at least one impeller is spaced a first distance from a bottom of the container and a second position in which the at least one impeller is spaced a second distance from the bottom of the container, wherein the second distance is greater than the first distance. In an embodiment, the extensible shaft includes a first shaft segment and a second shaft segment telescopically connected to the first shaft segment, wherein the at least one impeller is connected to the second shaft segment. In an embodiment, the agitator assembly further includes at least one biasing element configured to exert an axial biasing force on the second shaft segment to bias the extensible shaft to the second position. In an embodiment, the agitator assembly further includes a latch member configured to retain the extensible shaft in the first position, and an actuator associated with the latch member, wherein actuation of the actuator releases the latch member to effect movement of the extensible shaft from the first position to the second position under the axial biasing force of the at least one biasing element. In an embodiment, the at least one impeller includes a first impeller connected to the first shaft segment and a second impeller connected to the second shaft segment. In the first position one of the first shaft segment and the second shaft segment is received by the other of the first shaft segment and the second shaft segment, and in the second position one of the first shaft segment and the second shaft segment extends from the other of the first shaft segment and the second shaft segment. In an embodiment, the agitator assembly further includes a locking mechanism configured to retain the extensible shaft in the second position. In an embodiment, the locking mechanism is a bayonet mount. In an embodiment, the agitator assembly further includes a magnetic hub connected to the extensible shaft configured to be rotatably driven by a magnetic drive assembly of the mixing system. In an embodiment, the mixing system includes a rigid support vessel configured to receive the container, and the magnetic drive assembly associated with a bottom of the vessel, wherein the container is a flexible bioprocessing bag.

In another embodiment, an agitator assembly for a mixing system is provided. The agitator assembly includes a first shaft segment, a second shaft segment telescopically connected to the first shaft segment, and an impeller connected to the second shaft segment. The second shaft segment and impeller are moveable from a first position in which the second shaft segment is nested with the first shaft segment, and a second position in which the second shaft segment extends from the first shaft segment. In an embodiment, the agitator assembly further includes at least one biasing element configured to exert an axial biasing force on the second shaft segment to bias the second shaft member to the second position. In an embodiment, the agitator assembly includes a latch member configured to retain second shaft segment in the first position, and an actuator associated with the latch member, wherein actuation of the actuator releases the latch member to effect movement of the extensible shaft from the first position to the second position under the axial biasing force of the at least one biasing element. In an embodiment, the agitator assembly includes a second impeller connected to the first shaft segment. In an embodiment, the agitator assembly additionally includes a locking mechanism configured to retain the second shaft segment and the impeller in the second position. In an embodiment, the locking mechanism may be a bayonet mount. In an embodiment, the agitator assembly includes a magnetic hub connected to the first shaft segment and being configured to be rotatably driven by a magnetic drive assembly of a mixing system.

In yet another embodiment, a method for bioprocessing is provided. The method includes the steps of positioning a flexible bioprocessing bag inside a support vessel, the flexible bioprocessing bag containing an agitator assembly positioned at a bottom of the flexible bioprocessing bag, the agitator assembly including a hub, an extensible shaft connected to the hub, and an impeller connected to the extensible shaft, placing a hub of the agitator assembly in registration with a magnetic drive assembly exterior to the flexible bioprocessing bag, and extending the extensible shaft from a first position where the impeller is located a first distance from the bottom of the flexible bioprocessing bag, to a second position where the impeller is located a second distance from the bottom of the flexible bioprocessing bag, wherein the first distance is greater than the second distance. In an embodiment, extending the extensible shaft includes actuating an actuator to automatically effect movement of the extensible shaft from the first position to the second position. In an embodiment, the extensible shaft includes a first shaft segment and a second shaft segment telescopically connected to the first shaft segment, wherein the impeller is connected to the second shaft segment.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property.

This written description uses examples to disclose several embodiments of the invention, including the best mode, and also to enable one of ordinary skill in the art to practice the embodiments of invention, including making and using any devices or systems and performing any incorporated methods. The patentable scope of the invention is defined by the claims, and may include other examples that occur to one of ordinary skill in the art. Such other examples are intended to be within the scope of the claims if they have structural elements that do not differ from the literal language of the claims, or if they include equivalent structural elements with insubstantial differences from the literal languages of the claims.

What is claimed is:

1. A mixing system for a bioreactor system, comprising:
a container for containing a fluid; and
an agitator assembly disposable in the container for mixing the fluid, the agitator assembly including:
an extensible shaft having a plurality of nestable shaft segments and at least one impeller connected to the extensible shaft, wherein the plurality of nestable shaft segments are slidable with respect to one another so as to be configurable in a compact state; and
a spring element extending axially along the extensible shaft including the plurality of nestable shaft segments, wherein the spring element includes a plurality of shaft spring elements, each of the shaft spring elements configured to exert an axial biasing force on one of the plurality of nestable shaft segments to set an extended position, wherein each of the shaft spring elements extends axially along a length of a corresponding nestable shaft segment, wherein the shaft spring elements positioned about the corresponding nestable shaft segments in the extended position collectively extend axially along a length of the extensible shaft from near a bottom of the container to near a top of the container.

2. The mixing system of claim 1, wherein:
the extensible shaft is moveable between a first position in which the at least one impeller is spaced a first distance from the bottom of the container and a second position in which the at least one impeller is spaced a second distance from the bottom of the container;
wherein the second distance is greater than the first distance.

3. The mixing system of claim 2, wherein:
the plurality of nestable shaft segments of the extensible shaft includes a first shaft segment and a second shaft segment telescopically connected to the first shaft segment;
wherein the at least one impeller is connected to the second shaft segment.

4. The mixing system of claim 3, wherein:
one of the plurality of shaft spring elements is configured to exert an axial biasing force on the second shaft segment to bias the extensible shaft to the second position.

5. The mixing system of claim 4, wherein:
the agitator assembly further includes a latch member configured to retain the extensible shaft in the first position, and an actuator associated with the latch member;
wherein actuation of the actuator releases the latch member to effect movement of the extensible shaft from the first position to the second position under the axial biasing force of the one of the plurality of shaft spring elements.

6. The mixing system of claim 3, wherein:
the at least one impeller includes a first impeller connected to the first shaft segment and a second impeller connected to the second shaft segment; and
wherein in the first position, one of the first shaft segment and the second shaft segment is received by the other of the first shaft segment and the second shaft segment; and
wherein in the second position, one of the first shaft segment and the second shaft segment extends from the other of the first shaft segment and the second shaft segment.

7. The mixing system of claim 3, wherein:
the agitator assembly further includes a locking mechanism configured to retain the extensible shaft in the second position.

8. The mixing system of claim 7, wherein:
the locking mechanism is a bayonet mount.

9. The mixing system of claim 1, wherein:
the agitator assembly further includes a magnetic hub connected to the extensible shaft configured to be rotatably driven by a magnetic drive assembly of the mixing system.

10. The mixing system of claim 9, further comprising:
a rigid support vessel configured to receive the container; and
the magnetic drive assembly associated with a bottom of the vessel;
wherein the container is a flexible bioprocessing bag.

11. A method for bioprocessing, comprising the steps of:
positioning a flexible bioprocessing bag inside a support vessel, the flexible bioprocessing bag containing an agitator assembly positioned at a bottom of the flexible bioprocessing bag, the agitator assembly including a hub, an extensible shaft connected to the hub having a plurality of nestable shaft segments, a spring element extending axially along the extensible shaft including the plurality of nestable shaft segments that is configured to exert an axial biasing force on each of the nestable shaft segments, and an impeller connected to the extensible shaft;

placing the hub of the agitator assembly in registration with a magnetic drive assembly exterior to the flexible bioprocessing bag; and extending the extensible shaft from a first position where the impeller is located a first distance from the bottom of the flexible bioprocessing bag, to a second position where the impeller is located a second distance from the bottom of the flexible bioprocessing bag;

wherein the second distance is greater than the first distance, wherein the spring element includes a plurality of shaft spring elements, each of the shaft spring elements configured to exert an axial biasing force on one of the plurality of nestable shaft segments to set an extended position, wherein each of the shaft spring elements extends axially along a length of a corresponding nestable shaft segment, wherein the shaft spring elements positioned about the corresponding nestable shaft segments in the extended position collectively extend axially along a length of the extensible shaft from near the bottom of the flexible bioprocessing bag to near a top of the flexible bioprocessing bag.

12. The method according to claim 11, wherein:

extending the extensible shaft includes actuating an actuator to automatically effect movement of the extensible shaft from the first position to the second position.

13. The method according to claim 12, wherein:

the plurality of nestable segments of the extensible shaft includes a first shaft segment and a second shaft segment telescopically connected to the first shaft segment;

wherein the impeller is connected to the second shaft segment.

* * * * *